US005830475A

United States Patent [19]

Aldovini et al.

[11] Patent Number: 5,830,475

[45] Date of Patent: Nov. 3, 1998

[54] RECOMBINANT MYCOBACTERIAL VACCINES

[75] Inventors: Anna Aldovini; Richard A. Young, both of Winchester, Mass.

[73] Assignee: Whitehead Institute for Biomedical Research

[21] Appl. No.: 460,981

[22] Filed: Jun. 5, 1995

Related U.S. Application Data

[63] Continuation of Ser. No. 96,027, Jul. 22, 1993, Pat. No. 5,591,632, which is a continuation-in-part of Ser. No. 711,334, Jun. 6, 1991, abandoned, which is a continuation-in-part of Ser. No. 367,894, Jun. 19, 1989, abandoned, which is a continuation-in-part of PCT/US89/02962, Jul. 7, 1989 and a continuation-in-part of PCT/US90/03451, Jun. 18, 1990 said Ser. No. 711,334, is a continuation-in-part of Ser. No. 361,944, Jun. 5, 1989, Pat. No. 5,504,005, which is a continuation-in-part of Ser. No. 223,089, Jul. 22, 1988, abandoned, and Ser. No. 216,390, Jul. 7, 1988, abandoned, which is a continuation-in-part of Ser. No. 163,546, Mar. 3, 1988, abandoned, which is a continuation-in-part of PCT/US88/00614, Feb. 29 1988 said Ser. No. 223,089, is a continuation-in-part of Ser. No. 163,546, which is a continuation-in-part of Ser. No. 20,451, Mar. 2, 1987, abandoned.

[51] Int. Cl.[6] .......................... A61K 39/04; A61K 39/21; C12N 1/21

[52] U.S. Cl. .................... 424/200.1; 424/93.2; 424/93.4; 424/248.1; 424/282.1; 435/69.1; 435/172.3; 435/252.3; 435/253.1; 435/863; 435/864; 435/865; 435/866

[58] Field of Search ................................ 424/93.2, 200.1, 424/248.1, 93.4; 435/172.3, 69.1, 252.3, 253.1, 863, 864, 865, 866

[56] References Cited

PUBLICATIONS

Labidi et al., FEMS Microbiol. Lett., 30:221—225 (1985).

Labidi et al., Ann. Inst. Pasteur Microbiol., 136 B(2):209–215 (1985).

Jacobs et al., Nature, 327:532–535 (1987).

Norgard et al., J. Bacteriol., 133(3): 1254–1262 (1978).

Burke et al., EMBO J., 3(11): 2549–2554 (1984).

Lindquist et al., Ann. Rev. Genet., 22: 631–677 (1988).

Lathigra et al., Nucl. Acids. Res., 16(4): 1636 (1988).

Thole et al., Infec. and Immun., 55(6): 1466–1475 (1987).

*Primary Examiner*—George C. Elliott
*Assistant Examiner*—Johnny F. Railey, II
*Attorney, Agent, or Firm*—Hamilton, Brook, Smith & Reynolds, P.C.

[57] ABSTRACT

The present invention relates to recombinant mycobacteria, particularly recombinant *M. bovis* BCG, which express heterologous DNA encoding a product (protein or polypeptide) of interest, such a protein or polypeptide (e.g., an antigen) against which an immune response is desired, or a cytokine.

5 Claims, 10 Drawing Sheets

HSP60 promoter and polylinker (P)

hsp60Pr-ATG GCC AAG ACA ATT GCG GAT CCA GCT GCA GAA TTC GAA GCT TAT CGA TGT CGA CGT
BalI BamHI EcoRI HindII ClaI SalI Epitope tag sequence (T)

AatII
··· AGA TCT TCA CCA TAC GAC GTC CCA GAC TAC GCT GGA TCC TCT AGA GTC GAC —
BglII Influenza HA epitope tag 12CA5 BamHI XbaI SalI BCG alpha antigen signal sequence (SS)

BalI
ATG GCC ACA GAC GTG AGC CGA AAG ATT CGA GCT TGG GGA CGC CGA TTG ATG ATC
GGC ACG GCA GCG GCT GTA GTC CTT CCG GGC CTG GTG GGG CTT GCC
GGC GGA GCG GCA ACC GCG GGC GCG GGATCC
BamHI

FIG. 4A

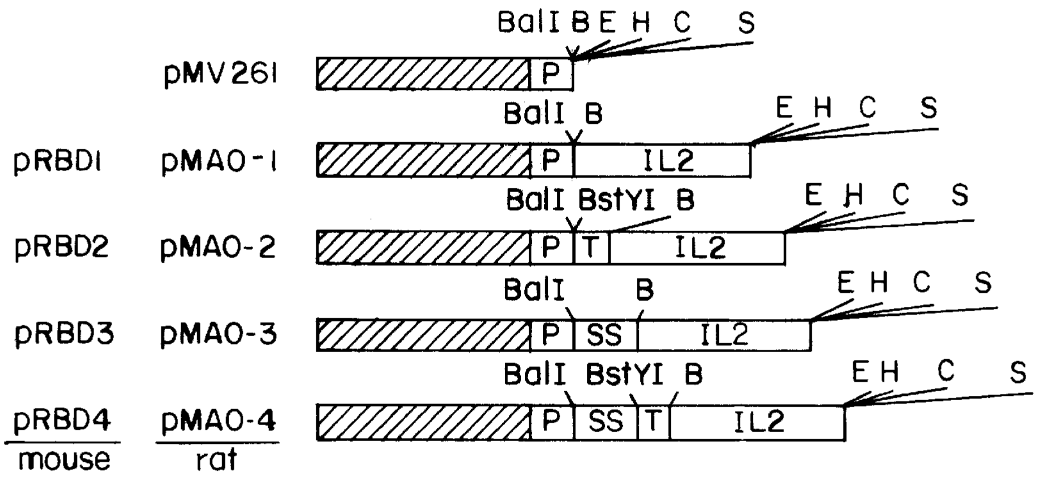

FIG. 4B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

ATGGCCAAGA CAATTGCGGA TCCAGCTGCA GAATTCGAAG CTTATCGATG TCGACGT 57

( 2 ) INFORMATION FOR SEQ ID NO:2:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:2:

AGATCTTCAC CATACGACGT CCCAGACTAC GCTGGATCCT CTAGAGTCGA C 51

( 2 ) INFORMATION FOR SEQ ID NO:3:

( i ) SEQUENCE CHARACTERISTICS:
( A ) LENGTH: 129 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

ATGGCCACAG ACGTGAGCCG AAAGATTCGA GCTTGGGGAC GCCGATTGAT GATCGGCACG 60

GCAGCGGCTG TAGTCCTTCC GGGCCTGGTG GGGCTTGCCG GCGGAGCGGC AACCGCGGGC 120

GCGGGATCC 129

( 2 ) INFORMATION FOR SEQ ID NO:4:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GGCATGGCCA AGGGATCCGC ACCCACTTCA AGCCCTGCA 39

( 2 ) INFORMATION FOR SEQ ID NO:5:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

CGGAATTCTT ACTGAGTCAT TGTTGAGATG AT 32

( 2 ) INFORMATION FOR SEQ ID NO:6:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

CAAGGGATCC GCACCCATTC AAGCCCTGCA 30

( 2 ) INFORMATION FOR SEQ ID NO:7:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

-continued ( x i ) SEQUENCE DESCRIPTION: SEQ ID NO:7:

GCCGGAATTC TTACTGAGTC ATTGTTGAGA TGAT 34

( 2 ) INFORMATION FOR SEQ ID NO:8:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

GCCATGCCAC AGACGTGAGC CGAAAGATTC GA 32

( 2 ) INFORMATION FOR SEQ ID NO:9:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:9:

GCCGGGATCC CGCGCCCGCG GTTGCCGCTC CGCC 34

RECOMBINANT MYCOBACTERIAL VACCINES

RELATED APPLICATIONS

This application is a continuation of application Ser. No. 08/096,027, filed Jul. 22, 1993, now U. S. Pat. No. 5,591, 632, which is a continuation-in-part of Ser. No. 07/711,334, filed Jun. 6, 1991, now abandoned, which is a continuation-in-part of Ser. No. 07/367,894, filed Jun. 19, 1989, now abandoned, said 07/711,334 is a continuation-in-part of PCT/US90/03451, filed Jun. 18, 1990 and a continuation-in-part of PCT/US89/02962, filed Jul. 7, 1989, which are both a continuation-in-part of Ser. No. 07/361,944, filed Jun. 5, 1989, now U.S. Pat. No. 5,504,005, which is continuation-in-part of Ser. No. 07/223,089, filed Jul. 22, 1998, now abandoned, and a continuation-in-part of Ser. No. 07/216, 390, filed Jul. 7, 1988, now abandoned, each of which is a continuation-in-part of Ser. No. 07/163,546, filed Mar. 3, 1988, now abandoned and PCT/US88/00614, filed Feb. 29, 1988, which is a continuation-in-part of Ser. No. 07/020, 451, filed Mar. 2, 1987, now abandoned. All of the above applications are incorporated herein in their entirety.

FUNDING

Work described herein was supported by the United States Public Health Service and the World Health Organization.

BACKGROUND

Several viral and bacterial live recombinant vaccine vehicles are being developed to produce a new generation of vaccines against a broad spectrum of infectious diseases (Bloom, B. R., *Nature* 342:115–120 (1989)). The human tuberculosis vaccine *Mycobacterium bovis* bacillus Calmette-Guerin (*M. bovis*-BCG or BCG) (Calmette et al., *Bull. Acad. Natl. Med.* (Paris) 91:787–796 (1924)) has features that make it a particularly attractive live recombinant vaccine vehicle. BCG and other mycobacteria are highly effective adjuvants, and the immune response to mycobacteria has been studied extensively. With nearly 2 billion immunizations, BCG has a long record of safe use in man (Luelmo, F., *Am. Rev. Respir. Dis.* 125:70–72 (1982) and Lotte et al., *Adv. Tuberc. Res.* 21:107–193 (1984)). It is one of the few vaccines that can be given at birth, it engenders long-lived immune responses with only a single dose, and there is a worldwide distribution network with experience in BCG vaccination.

To date, vaccines have been developed which, although effective in many instances in inducing immunity against a given pathogen, must be administered more than once and may be unable to provide protection, on a long-term basis, against a pathogen. In addition, in many cases (e.g., leprosy, malaria, etc.), an effective vaccine has yet to be developed.

DISCLOSURE OF THE INVENTION

The present invention relates to genetically recombinant (genetically engineered) mycobacteria which express DNA of interest which has been incorporated into the mycobacteria and is expressed extrachromosomally (episomally or autonomously) in the recombinant mycobacteria under the control of a mycobacterial heat shock protein (hsp) promoter, or stress protein promoter region (e.g., hsp70, hsp60). It particularly relates to recombinant *M. bovis*-BCG in which DNA of interest is expressed extrachromosomally under the control of a mycobacterial hsp promoter, such as hsp70 and hsp60. DNA of interest is heterologous DNA (i.e., DNA from a source other than the mycobacterium into which it is introduced) and is all or a portion of a gene or genes encoding protein(s) or polypeptide(s) of interest. The protein(s) or polypeptide(s) of interest can be, for example, those against which an immune response is desired (antigens), enzymes, cytokines, lymphokines and immunopotentiators.

The present invention further relates to vaccines which are genetically recombinant mycobacteria, particularly recombinant BCG, which express DNA of interest extrachromosomally under the control of a mycobacterial hsp promoter and induce an immune response (e.g., antibody production, T cell response) in mammals to whom they are administered. A BCG-HIV vaccine which is recombinant BCG which expresses at least one HIV-encoded polypeptide extrachromosomally under the control of a mycobacterial hsp promoter and induces an immune response to the polypeptide is a specific embodiment of the present invention.

The present invention further relates to a mycobacterial cytokine vaccine which is a recombinant mycobacterium which expresses and secretes a functional cytokine under the control of a mycobacterial hsp promoter and has been shown to induce endogenous cytokine production, resulting in stimulation of T cells and macrophages. In addition, the recombinant mycobacterium has been shown to be a more potent stimulator of T cells and macrophages than the mycobacterium alone (wild type). In a specific embodiment, the recombinant mycobacterium which expresses and secretes a functional cytokine is recombinant BCG. The recombinant BCG has been shown to induce endogenous cytokine production to a greater extent than wild type BCG. The recombinant BCG expressing a cytokine offer a novel means of enhancing the host (e.g., human and other mammalian) immune response to BCG.

The resulting recombinant mycobacteria are particularly useful as vehicles in which the DNA of interest can be expressed. Such vehicles can be used, for example, as vaccine vehicles which express a polypeptide or a protein of interest (or more than one polypeptide or protein), such as an antigen or antigens, for one or more pathogens of interest.

The recombinant mycobacteria can also be used as a vehicle for expression of cytokines, immunopotentiators, enzymes, pharmacologic agents and antitumor agents; expression of a polypeptide or a protein useful in producing an anti-fertility vaccine vehicle; or expression of stress proteins, which can be administered to evoke an immune response or to induce tolerance in an autoimmune disease (e.g., rheumatoid arthritis). Recombinant mycobacteria can, for example, express protein(s) or polypeptide(s) which are growth inhibitors or are cytocidal for tumor cells (e.g., interferon α, β or interleukins 1–7, tumor necrosis factor (TNF) α or β) and, thus, provide the basis for a new strategy for treating certain human cancers (e.g., bladder cancer, melanomas). Pathogens of interest include any virus, retrovirus, microorganism, or other organism or substance (e.g, a toxin or toxoid) which causes disease. The present invention also relates to methods of vaccinating a host with the recombinant mycobacterium to elicit protective immunity in the host. The recombinant vaccine can be used to produce humoral antibody immunity, cellular immunity (including helper and cytotoxic immunity) and/or mucosal or secretory immunity. In addition, the present invention relates to use of the polypeptide(s) or protein(s) such as antigens or cytokines, expressed by the recombinant cultivable mycobacterium as vaccines or as diagnostic reagents.

The vaccine of the subject invention has important advantages over presently-available vaccines. For example, mycobacteria have adjuvant properties among the best currently known and, thus, stimulate a recipient's immune system to respond to other antigens with great effectiveness. This is a particularly valuable aspect of the vaccine because it induces cell-mediated immunity and will, thus, be especially useful in providing immunity against pathogens in cases where cell-mediated immunity appears to be critical for resistance. Second, the mycobacterium stimulates long-term memory or immunity. As a result, a single (one-time) inoculation can be used to produce long-term sensitization to protein antigens. Using the vaccine vehicle of the present invention, it is possible to prime long-lasting T cell memory, which stimulates secondary antibody response neutralizing to the infectious agent or the toxin. This is useful, for example, against tetanus and diphtheria toxins, pertussis, malaria, influenza, herpes viruses and snake venoms. Recombinant BCG of the present invention which express a cytokine, such as IL-2, are particularly useful because of their enhanced immunostimulatory properties (relative to nonrecombinant or wild type BCG). The present invention is, thus, useful to augment the immunostimulatory properies of BCG in immunization and cancer therapy. Any of a variety of cytokines can be expressed in recombinant mycobacteria, especially recombinant BCG, of the present invention.

BCG in particular has important advantages as a vaccine vehicle in that: 1) it is the only childhood vaccine currently given at birth; 2) in the past 40 years, it has had a very low incidence of adverse effects, when given as a vaccine against tuberculosis; and 3) it can be used repeatedly in an individual (e.g., in multiple forms).

A further advantage of BCG in particular, as well as mycobacteria in general, is the large size of its genome (approximately $3\times10^6$ bp in length). Because the genome is large, it is able to accommodate a large amount of DNA from another source (i.e., DNA of interest) and, thus, can be used to make a multi-vaccine vehicle (i.e., one carrying DNA of interest encoding protective antigens for more than one pathogen).

BRIEF DESCRIPTION OF THE FIGURES

FIG. 4A is the DNA maps of the relevant portions of (1) HSP60 promoter and polylinker (SEQ ID No: 1) (2) Epitope tag sequence (SEQ ID NO:2), and (3) BCG alpha antigen signal sequence (SEQ ID NO: 3) used in construction of IL-2 containing *E. coli*-BCG shuttle plasmids.

FIG. 4B is a schematic illustration of IL-2 containing plasmid constructs with restriction sites; P=HSP60 promoter, T=Epitope tag, SS=BCG signal sequence; B=BamHI, E=EcoRI, H=HindIII, C=Cla I and S=Sal I.

DETAILED DESCRIPTION OF THE INVENTION

*Mycobacterium bovis*-BCG (bacillus Calmette-Guerin) is an important clinical tool because of its immunostimulatory properties. Cell wall extracts of BCG have proven to have excellent immune adjuvant activity. Recently developed molecular genetic tools and methods for mycobacteria have provided the means to introduce foreign genes into BCG (Jacobs, W. R., Jr., et al., *Nature* 327:532–535 (1987), Snapper, S. B., et al., *Proc. Natl. Acad. Sci. USA* 85:6987–6991 (1988), Husson, R. N., et al., J. Bacteriol 172:519–524) and Martin, C., et al., *Nature* 245:739–743 (1990)). Live BCG is an effective and safe vaccine used worldwide to prevent tuberculosis.

The present invention relates to recombinant mycobacteria, particularly recombinant *M. bovis* BCG, which express heterologous DNA encoding a product (protein or polypeptide) of interest, such a protein or polypeptide (e.g., an antigen) against which an immune response is desired or a cytokine. Recombinant *M. bovis* BCG of the present invention which express a cytokine or cytokines have enhanced immunostimulatory properties, in comparison with the immunostimulatory properties of *M. bovis* BCG which does not express a cytokine or cytokines. The enhanced immunostimulatory properties of recombinant BCG which expresses a cytokine or cytokines make that such recombinant BCG particularly useful as vaccines.

As described herein, it has now been shown that a variety of HIV1 polypeptides can be expressed in BCG recombinants under the control of a mycobacterial hsp promoter and that the foreign polypeptides produced in BCG induce antibody and T cell responses in mammals to which the recombinant mycobacteria are administered. These results demonstrate that BCG can be used as a live recombinant vaccine vehicle to induce immune responses to pathogen proteins produced by the bacillus. In particular it has been shown that HIV1 polypeptides are expressed in BCG recombinants under the control of the mycobacterial hsp70 promoter or similar mycobacterial promoter and induce immune responses to the encoded proteins in mammals to whom they are administered.

Figure 1A:
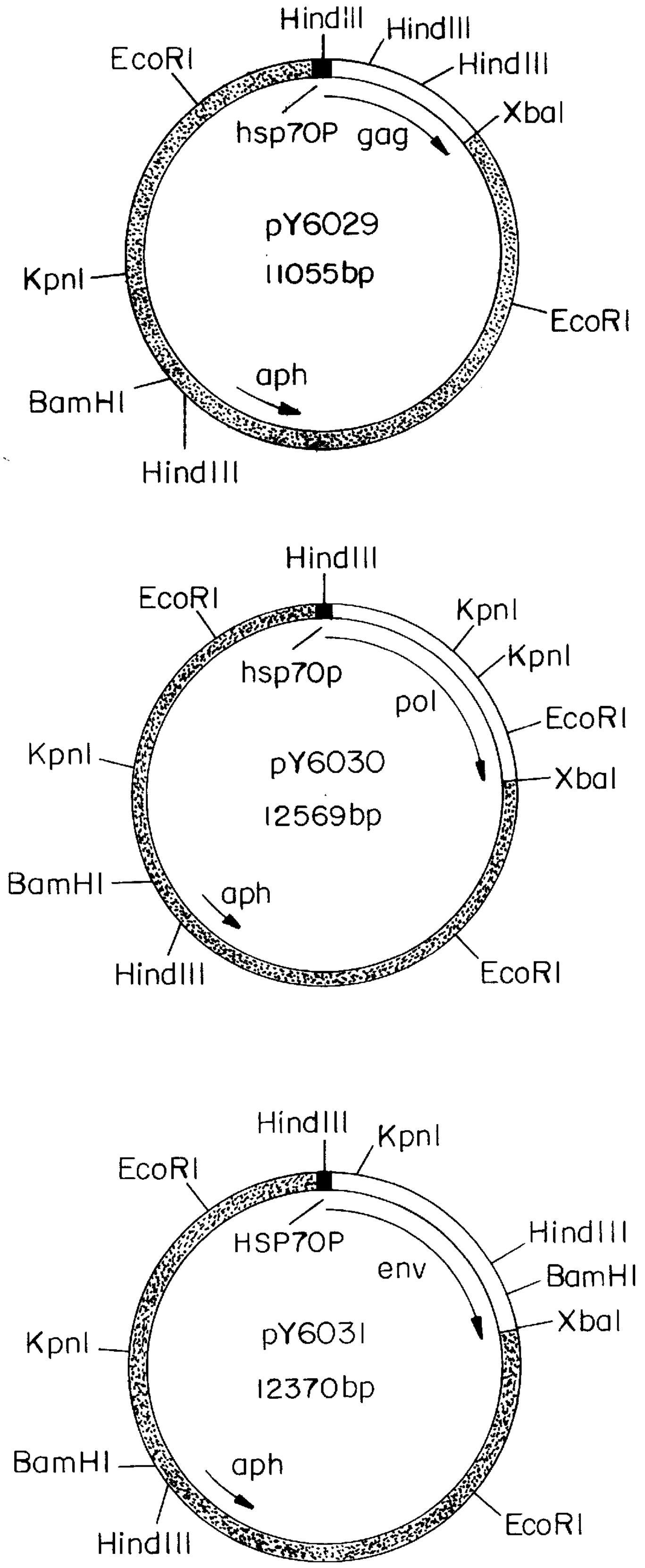
FIG. 1*a* illustrates the structures of plasmids pY6029, pY6030, and pY6031 which direct expression of HIV1 gag, pol and env polyproteins, respectively, under the control of the mycobacterial hsp70 promoter.

As described herein, three different HIV1 genes have been expressed in recombinant BCG, using a mycobacterial promoter and translational start site to direct the expression of the DNA of interest. These regulatory elements, and particularly the hsp70 promoter, were selected because they are among the most powerful in bacteria (Neidhardt, F. C., et al., In *Escherichia coli* and *Salmonella typhimurium*, Cellular and Molecular Biology), F. C. Neidhardt, e al., eds., Washington, DC: American Society for Microbiology, 1654 pp (1987)) and because hsp70 synthesis is induced to very high levels during phagocytosis of some bacteria by macrophage (Buchmeier et al., *Science* 248:730–732 (1990)). The hsp promoters also normally control the expression of proteins that are dominant antigens in the immune response to mycobacterial infection (Young, R. A., *Annu. Rev. Immunol.* 8:401–420 (1990), Lamb et al., *Molec. Biol. and Med.* 7:311–321 (1990), and Kaufmann, S. H. E., *Immunol. Today* 11:129–136 (1990)). DNA fragments encoding HIV1 gag, pol and env precursors were fused to the mycobacterial hsp70 promoter and translational start site so that they precisely replaced the hsp70 coding sequences, to produce hybrid genes which include HIV1 DNA, the mycobacterial hsp promoter and translational start site. The resulting hybrid genes were inserted into the BCG autonomous replicating plasmid vector pYUB12 (Snapper et al., *Proc. Natl. Acad. Sci. USA* 85:6987–6991 (1988)). (FIG. 1*a*), using known methods. The recombinant plasmids were introduced into the Pasteur strain of *M. bovis* BCG by electroporation ((Snapper et al., *Proc. Natl. Acad. Sci. USA* 85:6987–6991 (1988)).

Figure 1B:
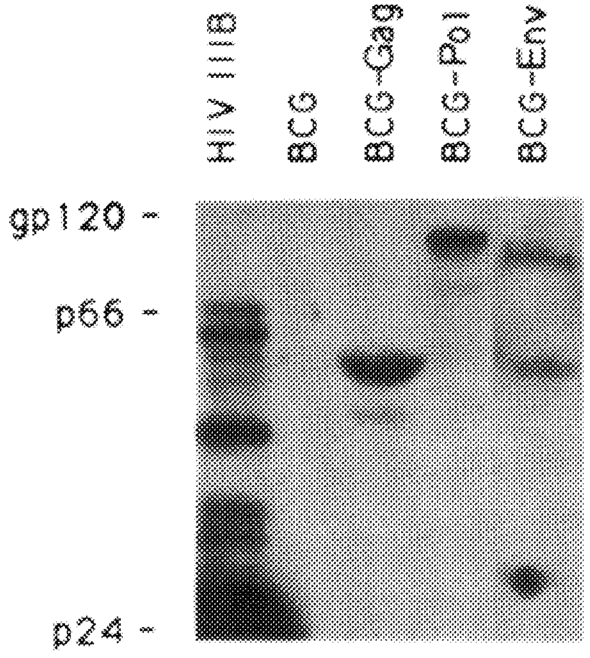
FIG. 1*b* is a Western blot illustrating the expression of the HIV1 gag, pol, and env gene products by *M. bovis* BCG electroporated with pY6029, pY6030, or pY6031.

The BCG recombinants produced HIV gag, pol, or env polyproteins when lysates of the bacteria were examined by Western blotting using serum from a HIV-1 positive individual (FIG. 1*b*). A 52 kD gag polypeptide was present in lysates of BCG cells containing the 1.53 kb gag gene, a 92 kD pol polyprotein was found in BCG carrying the 2.76 kb pol gene, and an 85 kD env polypeptide was detected in BCG containing the 2.56 kb env gene. The apparent molecular weight of each polyprotein was consistent with the size predicted by the gene sequence in the absence of post-translation modification (gag=512 aa, pol=922 aa, env=856 aa). By comparing the signal obtained with known amounts of HIV1 p24 with that obtained in lysates of BCG-HIV gag recombinants. The amount of full length gag precursor protein that accumulates in log-phase cells was estimated to be approximately 0.1% of total BCG protein. Proteolytic fragments of the HIV1 gag, pol and env precursor proteins were also detected. Thus, the total amount of HIV polypeptides that accumulate in the BCG recombinants may be considerably higher than 0.1% of total protein.

When present on the high copy pYUB12 plasmid, the hsp70 promoter is used constitutively at high levels in the absence of heat shock, as the HIV1 polyproteins did not accumulate to substantially higher levels after heat shock. In contrast, when integrated as a single copy in the BCG genome, lower levels of HIV1 gag are produced under the control of the hsp70 promoter at normal temperatures, and heat shock causes an increase in the accumulation of the foreign protein to levels similar to those found with the high copy autonomous vector (data not shown).

Figure 2:
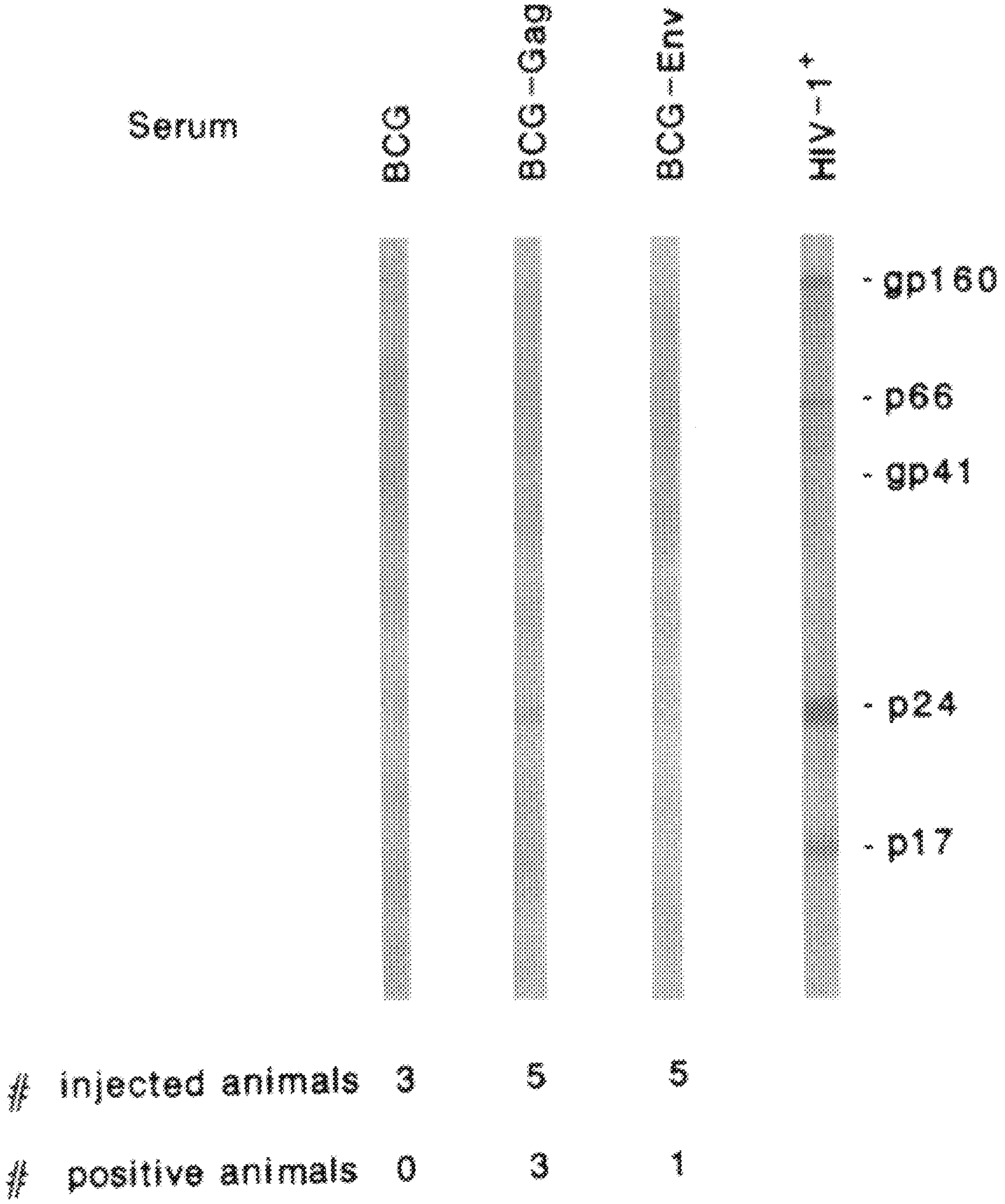
FIG. 2 shows a series of Western blot strips containing HIV proteins which were probed with serum from mice vaccinated with wild-type BCG; BCG-HIV gag recombinant cells or BCG-HIV env recombinant cells. The strip marked HIV1 was probed with human serum positive for HIV antibodies.

The ability of BCG recombinants to induce murine immune responses to the foreign proteins produced in BCG was also assessed. BALB/c mice were inoculated with one primary dose of $5\times10^6$ wild-type BCG, $5\times10^6$ BCG-HIV gag recombinants, or $5\times10^6$ BCG-HIV env recombinant bacilli to study antibody responses. The mice were inoculated intradermally or intravenously. Mice were bled 5 weeks after inoculation and their sera were used in ELISA and to probe Western blot strips containing HIV proteins (FIG. 2). Although none of the mice vaccinated with non-recombinant BCG had detectable antibodies to gag or env, 3 mice out of 5 vaccinated with BCG-HIV gag and 1 out of 5 vaccinated with BCG-HIV env had detectable levels of IgG antibodies reactive against gag (p24 and p17) and env (gp160) proteins. All of the mice that produced antibodies against HIV1 proteins had been inoculated with BCG recombinants intravenously. The levels of HIV-specific antibodies were generally low in the antibody-positive mice when tested by ELISA, and signals were detected when the sera were diluted no more than 1:50 in the Western blot assay. These results demonstrate that BCG recombinants can elicit antibody responses to foreign proteins produced by the bacillus.

Figure 3A:
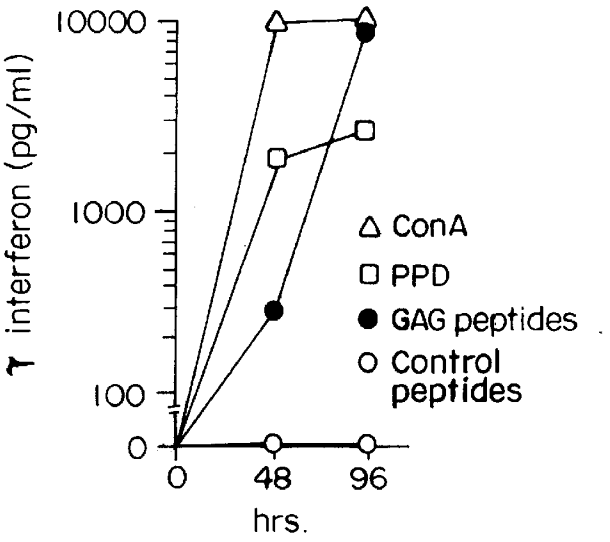
FIGS. 3*a*–3*e* is a series of graphs which illustrates the ability of BCG recombinants to induce cellular immune responses to a foreign pathogen. The levels of α-interferon (pg/ml) produced by spleen cells from mice inoculated with BCG-HIV gag recombinants (FIG. 3*a*) or nonrecombinant BCG (FIG. 3*b*) upon stimulation with 5 ug/ml *M. tuberculosis* purified protein derivative (PPD, squares), 10 ug/ml each of 5 peptides representing HIV1 gag amino acids 256–348 (filled circles), or 10 ug/ml each of 5 unrelated peptides (circles) is plotted against time after stimulation. The specific cytotoxic activity of total spleen cells (FIG. 3*c*), $CD8^+$ spleen cells (FIG. 3*d*), or $CD4^+$spleen cells (FIG. 3*e*) from mice immunized with BCG-HIV gag recombinants (continuous line) or with wild-type BCG (dashed lines) is also shown.
Figure 3B:
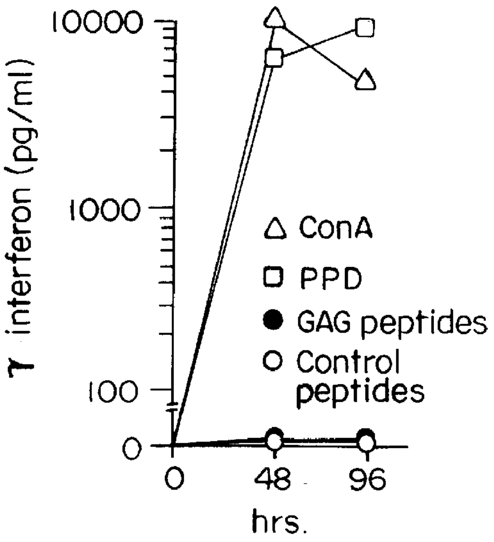

The ability of BCG recombinants to induce cellular immune responses to a foreign pathogen protein was investigated in mice inoculated with BCG-HIV gag recombinants, by measuring cytokine production and cytotoxic activity by spleen cells after stimulation with specific antigens. Cytotoxic T lymphocytes (CTL), and to a lesser extent Thl lymphocytes, produce γ-interferon when stimulated with specific antigens or with mitogens, and this response can be measured with clones or in bulk cultures (Mosmann et al., *Advances Immunol.* 46:111–147 (1989) and Swain et al., *J. Immunol.* 141:3445–3455 (1988)). Mice inoculated with recombinant BCG or with BCG-HIV gag were boosted with $5\times10^6$ BCG or with $5\times10^6$ BCG-HIV gag, respectively. Both HIV p24 protein, which is a processed segment of the gag polyprotein, and peptides covering the entire gag amino acid sequence were used as stimulating antigens in a γ-interferon production assay. Spleen cells from mice inoculated with BCG-HIV gag recombinants produced substantial levels of γ-interferon when stimulated with HIV1 gag peptides, but not when exposed to similar levels of unrelated polypeptides (FIG. 3*a*). The level of γ-interferon produced in response to stimulation with HIV1 gag peptides was similar to that obtained when cells were stimulated with HIV1 p24 (not shown) or with *M. tuberculosis* purifed protein derivative (PPD) or concanavalin a (ConA)(FIG. 3*a*). Spleen cells from mice inoculated with nonrecombinant BCG responded well to PPD and ConA but were nonresponsive to the HIV-gag peptides (FIG. 3*b*). The spleen cell populations that produced γ-interferon in response to specific antigens also produced IL-2, as measured in a proliferation assay (16) using the IL-2-dependent CTLL-2 cell line (not shown). Thl lymphocytes are believed to be the major source of IL2 in antigen stimulated spleen cell populations (Mosmann et al., *Advances Immunol.* 46:111–147 (1989) and Swain et al., *J. Immunol.* 141:3445–3455 (1988)). These results demonstrate that BCG recombinants can induce murine cell-mediated immune responses to a foreign protein produced by the BCG recombinants, and are consistent with the involvement of both CTL and Thl lymphocytes.

Figure 3C:
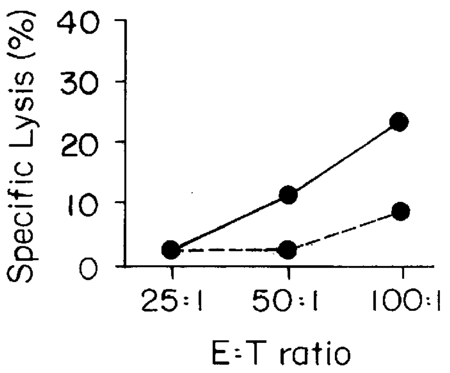
Figure 3D:
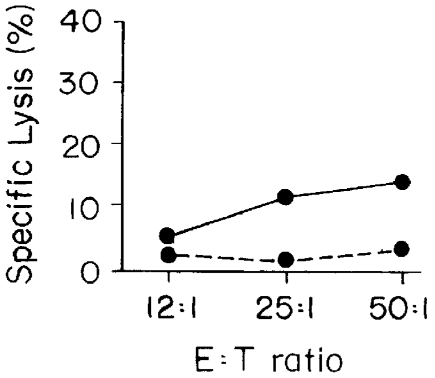
Figure 3E:
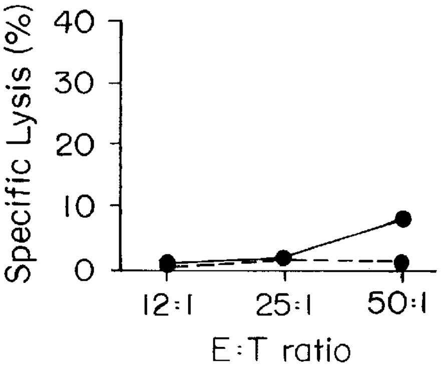

To investigate further the T cell response to the BCG-HIV gag recombinant, the antigen specific cytolytic activity of spleen cells and of spleen cells depleted of either CD4 or CD8 cells was measured in a $^{51}Cr$ release assay (Nagler-Anderson et al., *J. Immunol.* 141:3299–3305 (1988) and Walker, B. D. in *Techniques in HIV Research* (ed. Aldovini et al.) 201–210 (Stockton Press, New York, 1990)). Spleen cells from mice immunized with the BCG-HIV gag recombinant specifically lysed target cells pulsed with gag petides (FIG. 3*c*), as did spleen cells depleted of $CD4^+$cells (FIG. 3*d*). There was limited specific cytolysis with cells depleted of $CD8^+$ cells (FIG. 3*e*); similarly low levels of specific cytolysis were observed when bulk spleen cells were preincubated with a monoclonal antibody that blocks CD8 function. These results indicate that most of the antigen-specific cytotoxic cells in the spleen population express $CD8^+$.

Multiple segments of HIV1 gag protein have been shown to be immunogenic in mice inoculated with the BCG-HIV gag recombinants (Table 1). Six pools of HIV1 gag peptides, each pool containing five overlapping 25 amino-acid peptides, were used to stimulate spleen cells from mice inoculated with BCG-HIV gag recombinants or nonrecombinant BCG. All six pools of gag peptides stimulated substantial amounts of γ-interferon production, albeit to different levels, in spleen cells from mice injected intravenously with the BCG-HIV gag recombinants. Spleen cells from mice inoculated with nonrecombinant BCG did not respond to any of the HIV-gag peptides. Thus, the BCG-HIV gag recombinants consistently induced T cell responses to a variety of epitopes in the foreign protein.

In another embodiment of the present invention, recombinant mycobacteria, particularly recombinant BCG, containing DNA encoding a cytokine (e.g., IL-2) have been produced and shown to produce and secrete the cytokine in a biologically active form. As described in Example 4, genes encoding IL-2 were inserted into an *E. coli*-BCG shuttle plasmid under the control of a mycobacterial heat shock protein (hsp) promoter. *M. bovis* BCG recombinants were constructed that produce and secrete the mammalian cytokine IL-2 in a biologically active form. Secretion of the active cytokine was accomplished through the combined use of the BCG hsp60 promoter and a secretion signal sequence derived from the BCG alpha-antigen. The BCG recombinants that secrete IL-2 have been shown to stimulate the production of specific lymphokines by mouse splenocyte cultures to a greater extent than wild type BCG stimulated their production, thus demonstrating that BCG recombinants that express IL-2 and other cytokines are a more potent stimulus of T cells and macrophages than the wild type BCG and can be used to modify the levels of specific cytokine production.

An in vitro prototype cytokine expression system for BCG is demonstrated in Example 4. As described, IL-2 encoding sequences are fused with the BCG alpha antigen signal sequence, resulting in expression and extracellular accumulation of biologically active IL-2. Additional evidence that the signal peptide was responsible for secretion was found in the Western blot analysis of the BCG recombinants. For each of the BCG recombinants that incorporated the signal sequence, the expressed IL-2 polypeptide appeared to accumulate in BCG cells both with and without the signal peptide; in contrast, the size of the single secreted form of IL-2 was consistent with that expected for IL-2 after the signal peptide has been cleaved. Matsuo et al., previously demonstrated that HIV epitopes fused to the full length alpha antigen from *Mycobacterium kansasii* were secreted with the modified protein after signal peptide cleavage (Matsuo et al., *Infect. Immun.* 58:4049–4054 (1990)). However, there are no previous reports that the BCG alpha antigen signal peptide itself could direct the extracellular secretion of a full length cloned protein from BCG.

The selection of the cytokine IL-2 as the first recombinant cytokine to be tested for secretion from BCG was based on the known central role of T cell mediated immune responses to BCG infection (Ratliff et al., *J. Urol.* 17:155–158 (1987)). An in vitro model of immune stimulation was developed using a mixed population of lymphocytes derived from spleen cells to determine if IL-2 secreting BCG would specifically affect a particular subset of T cells. A modest amount of γ-interferon production by naive splenocytes in response to BCG was found. IL-4 and IL-5 production, however, remained undetectable. This pattern of cytokine secretion by BCG is consistent with preferential T helper type one (TH-1) activation (Cherwinski et al., *J. Exp. Med.* 166:1229–1244 (1987)). A preferential stimulation of TH-1 cells has been described in splenocytes from C57BL/6 mice previously immunized with BCG or Leishmania Major (Chatelain et al., *J. Immunol.* 148:1182–1187 (1992)) and has been linked to major histocompatibility immune response genes (Huygen et al., *Infect. Immun.* 60:2880–2886 (1992) and Heinzel et al., *J. Exp. Med.* 169:59–72 (1989)).

The most dramatic results from the splenocyte assay were revealed for the IL-2 secreting BCG recombinant. Both IFN-γ and IL-2 production by splenocytes were increased approximately 7–8 fold over that produced by naive splenocytes treated with BCG alone. The effect on IFN-γ production was clearly synergistic, since BCG alone, IL-2 alone, nor the simple summation of their responses was able to generate such high levels. The production of IL-6 and TNF-α were also increased although to a much lesser extent. A remarkable finding, however, was the capacity of IL-2 secreting BCG to increase IFN-γ production from naive splenocytes to a level well beyond that found for splenocytes treated with BCG alone. This effect was clearly related to the presence of IL-2 as it could be reproduced by the addition of exogenous IL-2 to wild type BCG. Furthermore, neutralizing antibody to IL-2 blocks this response. A synergistic increase in IFN-γ was shown to occur across 3 different mouse strains, supporting the concept that the local cytokine environment at the time of antigen presentation can significantly influence the direction and amplitude of the immune response. This is particularly significant for the BALB/c strain which characteristically is a poor IFN-γ producer (Heinzel et al., *J. Exp. Med.* 169:59–72 (1989)). These results suggest that this recombinant BCG might be expected to have enhanced adjuvant and immunostimulatory properties above that found in wild type BCG. The modifications described herein whereby BCG is engineered to provide a source of biologically active cytokines represents a novel means to enhance the host immune response to BCG therapy and study its mechanism of action.

The adjuvant properties of BCG and its cell wall components have previously been exploited in experimental vaccines in animals and in man. For example, mixtures of BCG and specific schistosomal antigens have been used to successfully protect mice in a model of schistosomiasis (Pierce et al., *Proc. Natl. Acad. Sci. USA* 85:5678–5682 (1988)). An adjuvant/antigen mixture of muramyl dipeptide (MDP) and killed simian immunodeficiency virus (SIV) have provided partial protection against SIV infection in macaques (Desrosiers et al., *Proc. Natl. Acad. Sci. USA* 36:6353–6357 (1989) and Murphey-Corb et al., *Science* 246:1293–1297 (1989)); MDP is one of the components of mycobacterial cell walls that contributes to the adjuvant properties of BCG. Humans have been vaccinated with mixtures of BCG and killed *Mycobacterium leprae* in large scale trials to assess the efficacy of this leprosy vaccine candidate (Bloom, B. R., *J. Immunol.* 137:i–x (1986)).

As shown herein, recombinant BCG vaccine vehicles can induce immune responses to foreign proteins produced by the bacillus, indicating that BCG can act simultaneously as an adjuvant and as a vehicle to produce and deliver selected antigens to the immune system. The ability to engineer BCG to produce one or more foreign pathogen antigens has several advantages over mixtures of mycobacterial adjuvant and pathogen antigens. Because the antigen continues to be produced by BCG replicating in vivo, a BCG recombinant may provide a more long-lived immune response to the pathogen of interest than that provided by the simple mixture of BCG and antigen. It may be more cost-effective to engineer BCG recombinants than to produce the mixture. Perhaps most importantly, the ease with which bacteria can be manipulated genetically makes it possible that features of the BCG vaccine vehicle can be tailored to maximize the desired immune responses. In addition, as demonstrated herein, recombinant BCG can be used as a vaccine vehicle to express and secrete functional cytokines which induce endogenous cytokine production in cells.

Thus, as described herein, recombinant mycobacterium in which DNA of interest is expressed extrachromosomally under the control of a mycobacterial hsp promoter have been shown to elicit immune responses to the proteins produced therein in mammals to which they are administered. They have been shown to elicit an antibody response and to induce cell-mediated immune responses to the protein encoded by the DNA of interest.

As also described herein, recombinant mycobacteria, particularly recombinant *M. bovis* BCG, which express a cytokine (e.g., IL-2) or have been produced and shown to have augmented or enhanced immunostimulatory properties, when compared with *M. bovis* BCG. which does not express the cytokine.

Recombinant mycobacteria of the present invention can be used, for example, as vaccines to induce immunity against the pathogenic antigen encoded by the DNA of interest. A pathogen is any virus, microorganism, or other organism or substance (e.g., toxins) which causes disease. A vaccine vehicle useful for immunizing against leprosy can be made. Because of the extraordinary adjuvant activity of mycobacteria, such as BCG, such a vaccine would be effective in producing cell-mediated immunity, particularly of a long-term or enduring nature.

Vaccine vehicles which express a protein antigen or antigens from malaria sporozoites, malaria merozoites, diphtheria toxoid, tetanus toxoid, Leishmania, Salmonella, *Mycobacterium africanum, Mycobacterium intracellulare, Mycobacterium avium*, treponema, pertussis, herpes virus, measles virus, mumps, Shigella, Neisseria, Borrelia, rabies, polio virus, Simian immunodeficiency virus (SIV), snake venom, insect venom or vibrio cholera can also be produced in a manner similar to that described for HIV1.

The present invention further pertains to vaccine vehicles which express and secrete cytokines which induce production of endogenous cytokines. In principle, any cytokine gene derived from any source can be introduced and expressed in BCG. The modified *E. coli*-BCG shuttle vectors described herein can be used to express and secrete any of a variety of cytokines. The expression of epitope tagged cytokines from some of these vectors provides an additional assay for the presence of the cytokine. By being able to descriminate between the recombinant cytokine produced by BCG and the cytokine produced by mammalian cells, a more accurate picture of the mechanism of enhanced immunological stimulation can be obtained. In this embodiment, the DNA construct (e.g., *E. coli*-BCG shuttle plasmid) is comprised of the DNA of interest, a promoter and a secretion signal sequence wherein the 5' to 3' order is the promoter, the secretion signal sequence and the DNA of interest, and the DNA of interest is under the control of the promoter. The DNA construct can additionally comprise an epitope tag for detecting the DNA of interest.

Components of the plasmid introduced into BCG or other mycobacterium (e.g., DNA of interest, hsp promoter and translational start site) can be obtained from sources in which they naturally occur or can be synthesized, using known techniques, to have substantially the same sequence as the naturally-occurring equivalent. For example, they can be produced by genetic engineering techniques (e.g., cloning), by the polymerase chain reaction or synthesized chemically.

It is also possible, using the method of the present invention, to construct a multipurpose or multifunctional vaccine (i.e, a single vaccine vehicle which contains and expresses DNA of interest which includes more than one gene, such as a gene encoding a protein antigen for a different pathogen or toxin and genes encoding a cytokine). For example, it is possible to introduce into BCG a gene encoding a protein antigen for *M. lepare*, a gene encoding a protein antigen for *M. tuberculosis*, a gene encoding a protein antigen for Leishmania, a gene encoding a protein antigen for malaria and a gene encoding mammalian IL-2. Administration of this multi-valent vaccine would result in stimulation of an immune response to each antigen as well as a more potent stimulation of T cells and macrophages and provide long-term protection against leprosy, tuberculosis, leishmaniasis, and malaria.

The recombinant mycobacteria can also be used as an anti-fertility “vaccine” vehicle. For example, mycobacteria containing DNA encoding proteins such as human gonadotropic hormone (HGH) fragments, can be used as an anti-fertility vaccine and administered as a birth control agent. Vaccine vehicles of the present invention can be used to treat human cancers, such as bladder cancers or melanomas (e.g., by expressing growth inhibitors or cytocidal products). In this context, recombinant mycobacteria which contain and express cytokines (e.g., interferon α, β and/or γ, one or more interleukin (interleukins 1–7) and/or TNF α or β) are particularly useful. In another application, recombinant mycobacteria can be used to express stress proteins, either for the purpose of eliciting a protective immune response (e.g., against subsequent or long-term infection) or for the purpose of inducing tolerance in an autoimmune disease (e.g., rheumatoid arthritis). Stress proteins, such as those described in co-pending U.S. patent application Ser. No. 207,298, entitled Stress Proteins and Uses Therefore, by Richard A. Young and Douglas Young, filed Jun. 15, 1988, can be used for this purpose. Because of their large genomes (e.g., the BCG genome is about $3\times10^6$ bp long), mycobacteria can accommodate large amounts of DNA of interest, and thus, can serve as multi-purpose vehicles.

Recombinant mycobacteria of the present invention can be administered by known methods. They can be administered by a variety of routes, such as intradermally or intravenously. They can be administered alone to produce a desired response, such as an immune response, or can be administered in combination with the antigen(s) encoded by the DNA of interest and/or the killed or attenuated pathogen (s) against which an immune response is desired, in order to enhance or modify the resulting response.

The present invention will now be illustrated by the following examples, which are not to be considered limiting in any way.

Example 1

Expression of HIV1 genes in BCG using the Mycobacterial hsp70 Promoter and Ribosome Binding Site.

Construction of pY6029, pY6030 and pY6031.

Three different plasmids containing either the HIV gag, pol or env open reading frames were constructed. DNA fragments containing the coding sequence for HIV1 gag, pol, and env were synthesized by Polymerase Chain Reaction (PCR), using the plasmid pHXB2 (Fisher et al., *Nature* 316:262–265 (1985)) as a template, and using oligonucleotide primers specific for each gene. The upstream primers contained an NcoI site that overlapped the AUG translation initiation codon of each HIV1 gene, and the downstream primer contained an XbaI site immediately after the translation stop codon.

To attach the mycobacterial hsp70 promoter and ribosome binding site to each HIV1 gene, a pUC18 plasmid containing a 1.8 kb segment of the *M. tuberculosis* hsp70 gene (pY6013) was digested with NcoI and XbaI to remove the hsp70 protein coding sequence (the hsp70 ATG translation initiation codon sequence overlaps an NcoI site), leaving the ATG and 155 bp of upstream hsp70 promoter sequence. The vector DNA containing the hsp70 promoter was gel purified and ligated to the NcoI/XbaI PCR-derived HIV1 DNA fragments. The HIV1 genes and their associated mycobacterial regulatory sequences were each transferred from the pUC18 vectors to the mycobacterial autonomous replication plasmid vector pYUB12 (6): EcoRI-XbaI fragments, blunt-ended at the EcoRI site, were gel purified from the first set of plasmids and were inserted between the EcoRV and the XbaI sites of pYUB12 to produce pY6029 (containing HIV1 gag), pY6030 (containing HIV1 pol) and pY6031 (containing HIV1 env shown in FIG. 1*a*). All manipulations followed previously described procedures (Maniatis et al., J. Molecular cloning: a laboratory manual. Cold Spring Harbor Laboratory, Cold Spring Harbor, N.Y. (1982)).

Expression of HIV gag, pol or env Polyproteins in *M. bovis* BCG.

Plasmids pY6029, pY6030 or pY6031 were introduced into the Pasteur strain of *M. bovis* BCG by electroporation and cells were plated on Middlebrook-7HlO agar (Difco) supplemented with albumin dextrose complement (Difco), 0.25% tween 20, and ug/ml of kanamycin sulfate. After growth for three weeks at 37° (BCG cells have a doubling time of 24 hours), individual colonies were picked and expanded in suspension cultures in Middlebrook-7H9 broth (Difco) to mid-log phase. Aliquots of cells (1.5 ml) were harvested by centrifugation and pelleted cells were resuspended in 50 ul Laemli buffer (Laemli, U. K. *Nature* 227:680–685 (1970)), sonicated with three 20 second pulses using a microtip sonicator, and incubated at 100° D for 4 min. Debris was pelleted by microfuge centrifugation for 2 min. and 15 ul of each lysate was subjected to 10% SDS PAGE. The separated proteins were transferred from the gel to a nitrocellulose membrane and probed with human serum positive for HIV antibodies, followed by $^{123}$I-labeled >Protein A as described in Aldovini, A. and Young R. A., *J. Virol.*, 64:1920–1926 (1928). The X-ray film was exposed for 20 hrs., except for lane 5 (BCG-env), which was exposed for 60 hrs.

The results of the Western blot analysis of lysates of BCG recombinants probed with HIV-positive human serum is shown in FIG. 1*b*. From left to right, the lanes contain: (1) an HIV1 lysate containing 150 ng p24 protein (HIV IIIB); (2) a lysate of wild type *M. bovis* BCG (BCG); (3) a lysate of *M. bovis* BCG recombinants expressing HIV gag from pY6029 (BCG-gag); (4) a lysate of *M. bovis* BCG recombinants expressing HIV pol from pY6030 (BCG-pol); and (5) a lysate of *M. bovis* BCG recombinants expressing HIV env from pY6031 (BCG-env).

Example 2

Murine Antibody Response to Vaccination With BCG Recombinants Expressing HIV1 aag and env.

BALB/c mice were inoculated intradermally or intravenously with one primary dose of $5\times10^6$ wild-type BCG bacilli, $5\times10^6$ BCG-HIV gag recombinant bacilli or $5\times10^6$ BCG-HIV env recombinant bacilli. Mice were bled 5 weeks after inoculation, and the sera were used to probe Western blot strips of HIV1 proteins (DuPont).

Results of this analysis are shown in FIG. 2. From left to right the lanes were probed with: (1) serum from a mouse injected with nonrecombinant BCG (BCG); (2) serum from a mouse injected with a BCG recombinant expressing HIV gag (BCG-gag); (3) serum from a mouse injected with a BCG recombinant exrpessing HIV env (BCG-env); and (4) a human serum positive for HIV antibodies (HIV1+). The number of animals injected with BCG, or BCG-HIV gag or BCG-HIV env recombinants, and the number of animals with positive sera is indicated at the bottom of each lane.

Example 3

Murine T Cell Response to Inoculation With BCG-HIV gag Recombinants

The ability of BCG recombinants to induce cellular immune responses to a foreign pathogen protein in mice inoculated with BCG-HIV gag recombinants was investigated by measuring cytokine production and cytotoxic activity by spleen cells after stimulation with specific antigens.

BALB/c mice initially injected with $5\times10^6$ nonrecombinant BCG or BCG-HIV gag recombinants were boosted with a similar dose at 4 weeks and then at 8 weeks. Spleens were removed at week 9 and cells were cultured and tested for γ-interferon production as described (Wyler et al., *J. Immunol.* 138:1246–1249 (1987)). Spleen cells were stimulated at a concentration of $10^7$ cells/ml with antigen or mitogen and supernatants were removed 48 hrs. and 96 hrs. later. Levels of γ-interferon in the supernatants were measured in duplicate with a solid-phase enzyme-immunoassay (Genzyme). Supernatants were diluted where necessary to obtain γ-interferon values within the linear range of the assay (256–4100 pg/ml); the background cutoff value was 100 pg/ml. A set of thirty overlapping HIV1 gag peptides covering the entire gag sequence (Ratner et al., *Nature* 313:277–284 (1985)) was used for antigenic stimulation. Peptides were grouped in 6 pools of 5 peptides each, and used at a concentration of 10 ug/ml per peptide for stimulation.

The results of stimulation with one of the six pools of HIV gag peptides, representing amino acids 256–348 or with a pool containing 5 unrelated peptides as a negative control are shown in FIGS. 3*a* and 3*b*. FIGS. 3*a* and 3*b* show levels of γ-interferon produced by spleen cells from mice inoculated with BCG-HIV gag recombinants (FIG. 3*a*) or nonrecombinant BCG (FIG. 3*b*) after stimulation with 50 ug/ml PPD (squares), 5 ug/ml ConA (triangles), HIV-gag peptides (10 ug/ml each; filled circles) and control peptides (10 ug/ml each; circles). Levels of γ-interferon production were ascertained for 3 mice inoculated intravenously with BCG-HIV gag recombinants and 3 mice inoculated intravenously with nonrecombinant BCG. The results shown in a and b were obtained from one mouse in each group; the other two mice in each group have similar results.

Table 1 shows that multiple segments of HIV1 gag protein are immunogenic in mice inoculated with BCG-HIV gag recombinants. Spleen cells were obtained from 3 mice inoculated with BCG-HIV gag recombinants, 3 mice injected with nonrecombinant BCG were pooled, as were cells from the untreated mice. The results for stimulation of spleen cells from the three mice injected with BCG-HIV gag recombinants are recorded separately in Table 1.

The cells ($10^7$/ml) were stimulated with various peptides and γ-interferon levels (pg/ml) in cell supernatants were measured in a solid-phase enzyme-immunoassay (Genzyme) 4 days later (Wyler et al., *J. Immunol.* 138:1246–1249 (1987)), as described above. Supernatants were diluted 1:10 where necessary to obtain γ-interferon values within the linear range of the assay (256–4100 pg/ml), and values below 100 pg/ml were considered negative. Thirty overlapping HIV1 gag peptides (25 amino acids each and containing 8 overlapping amino acid residues) covering the entire gag sequence (Ratner et al., *Nature* 313:277–284 (1985)) were grouped in 6 pools of 5 peptides each, and used at a concentration of 10 ug/ml per peptide for stimulation. Five unrelated peptides were pooled and used at similar concentrations as a negative control.

To investigate antigen specific cytolytic activity in stimulated spleen cells from immunized mice, $CD8^+$ and $CD4^+$ T cell populations were purified from total spleen cells by two rounds of negative selection (with complement and with either anti-CD4 or anti-CD8 antibodies) and characterized by two color FACS analysis [FITC-labeled mAb to CD8 (53-6.7, rat IgG2a, Becton Dickinson) and phycoerythrin-conjugated mAb to CD4 (GK1.5, rat IgG2b, Becton Dickinson)] as described (Nagler-Anderson et al., *J. Immunol.* 141:3299–3305 (1988)). The FACS analysis demonstrated that the $CD8^+$ and $CD4^+$ T cell populations were contaminated less than 1% by cells of the other phenotype. Target cell lysis by total spleen or purified $CD8^+$ and $CD4^+$ T cells was measured by the standard 4-hr $^{51}Cr$ release assay (Walker, B. D. in *Techniques in HIV Research* (ed. Aldovini et al) 201–210 (Stockton Press, New York, 1990)). Target cells were generated by incubating P815 tumor cells (American Type Culture Collection) with HIV gag peptides at a concentration of 5 ug/ml per peptide and labelling with $^{51}Cr$. In each assay $10^4$ target cells were incubated with varying numbers of effector cells. Percentage specific $^{51}Cr$ release was calculated from 100 X(a-b)/(t-b), where a is $^{51}Cr$ release in the presence of effector cells, b is the spontaneous release from labeled target cells in the absence of effector cells and t is the total $^{51}Cr$ content of the target cells (released by the addition of 1% Nonidet P-40).

The results of this analysis are summarized in FIG. 3, in which the specific cytotoxic activity of total (FIG. 3*c*), $CD8^+$ (FIG. 3*d*) and $CD4^+$ (FIG. 3*c*) spleen cells from mice immunized with the BCG-HIV gag recombinant (continuous line), and from mice injected with wild type BCG (dashed line) is shown.

TABLE 1

| | Production of γ-interferon (pg/ml) by spleen cells stimulated with HIV gag peptides. | | | | | | |
|---|---|---|---|---|---|---|---|
| Injection | 1–93 | 86–178 | 171–263 | 256–348 | 341–433 | 426–512 | Control Peptides |
| BCG-HIV gag$^{(1)}$ | 3500 | 800 | 540 | >8200 | 800 | 510 | 0 |
| BCG-HIV gag$^{(2)}$ | 390 | 640 | 280 | 140 | 220 | 4050 | 0 |
| BCG-HIV gag$^{(3)}$ | 0 | 0 | 0 | 140 | 140 | 860 | 0 |
| BCG | 0 | 0 | 0 | 0 | 0 | 0 | 0 |
| None | 0 | 0 | 0 | 0 | 0 | 0 | 0 |

TABLE 1-continued

| | Production of γ-interferon (pg/ml) by spleen cells stimulated with HIV gag peptides. | | | | | | |
|---|---|---|---|---|---|---|---|
| Injection | 1–93 | 86–178 | 171–263 | 256–348 | 341–433 | 426–512 | Control Peptides |

Spleen cells were obtained from 3 mice inoculated with BCG-HIV gag recombinatns, 3 mice were injected with nonrecombinant BCG and 3 untreated mice; spleen cells from mice injected with nonrecombinant BCG were pooled, as were cells from the untreated mice. The cells ($10^7$/ml) were stimulated with varius peptides and γ-interferon levels (pg/ml) in cell supernatants were measured in a solid-phase enzyme-immunoassay (Genzyme) 4 days later (23), as described in FIG. 3 legend. Supernatants were diluted 1:10 where necessary to obtain γ-interferon values within the linear range of the assay (256–4100 pg/ml), values below 100 pg/ml were considered negative. Thirty overlapping HIV1 gag peptides (25 amino acids each and containing 8 overlapping amino acid residues) covering the entire gag sequence (24) were grouped in 6 pools of 5 peptides each, and used at a concentration of 10 μg/ml per peptide for stimulation. Five unrelated peptides were pooled and used at similar concentrations as a negative control.

Example 4

Recombinant BCG Secreting Functional Interleukin IL-2 Modulates Production of Splenocytes

Materials and Methods

Oligonucleotide Primers, Plasmid DNAs and Bacterial Strains.

Three sets of paired oligonucleotide primers were utilized in the polymerse chain reaction (PCR) with appropriate templates to produce insert DNAs with ends suitable for cloning in the plasmid pMV261. The oligonucleotide primers were:

for the rat IL-2 gene:

#1: GGCATGGCCAAGGGATCCGCACCCACTTCAAGCCCTGCA (SEQ ID NO: 4);
#2: CGGAATTCTTACTGAGTCATTGTTGAGATGAT (SEQ ID NO: 5);

for the mouse IL-2 gene:

#3: CAAGGGATCCGCACCCATTCAAGCCCTGCA (SEQ ID NO: 6);
#4: GCCGGAATTCTTACTGAGTCATTGTTGAGATGAT (SEQ ID NO: 7);

for the alpha antigen signal sequence:

#5: GCCATGCCACAGACGTGAGCCGAAAGATTCGA (SEQ ID NO: 8);
#6: GCCGGGATCCCGCGCCCGCGGTTGCCGCTCCGCC (SEQ ID NO: 9).

The rat and mouse IL-2 upstream primers #1 (SEQ ID NO: 4) and #3 (SEQ ID NO: 6) respectively were constructed to anneal with the IL-2 coding regions starting at codon 21 thereby excluding their native signal peptide regions. The BCG alpha antigen downstream primer 14 (SEQ ID NO: 7) terminated at the sequence encoding the putative protease cleavage site ala-gly-ala (Terasaka et al, Complete nucleotide sequence of immunogenic protein MPB70 from *Mycobacterium bovis* BCG. FEMS Lett. 58:273–276 (1989)) (FIG. 4A).

The rat IL-2 CDNA containing plasmid pRIL-2.8 was provided by A. McKnight and the mouse IL-2 cDNA plasmid pmut-1 was obtained through the ATCC (McKnight et al., *Immunogen* 30:145–147 (1989) and Yokota et al., *Proc. Natl. Acad. Sci. USA* 82:68–72 (1984)). The *E. coli*/BCG shuttle plasmid pMV261 was kindly provided by C. K. Stover (Stover et al., *Nature* 351:456–460 (1991)). The influenza hemagglutinin epitope tag sequence (HA tag) is described in Kolodziej, P. A. and Young, R. A., *Methods Enzymol.* 194:508–519 (1991) and had been cloned in the Bgl II and Bam HI sites of pSP72. (Promega)

*E.* coli MBM 7070 was obtained from Michael Seidman. *Mycobacterium bovis* BCG (Pasteur) obtained from ATCC was grown in 7H9 media containing 10% albumin dextrose solution (Difco) and 0.05% tween 80 (Sigma). Genomic BCG DNA was isolated by protease K digestion and phenol/chloroform extraction.

Construction of IL-2 expression vectors and BCG IL-2 recombinant strains. A schematic representation of the plasmids constructed for this study is given in FIG. 4B. The plasmid pMAO-1 was constructed by placing the appropriate Bal I/Eco RI digested rat IL-2 PCR insert into the similarly restricted parental plasmid, pMV261 (FIG. 4B). The plasmid pMAO-2 was obtained by first cloning the Bam HI/Sal I insert from pMAO-1 into the HA tag containing plasmid (FIG. 4A) and then placing the resulting BglII/EcoRI insert into the Bam HI/Eco RI site of pMV261. The plasmid pMAO-3 was constructed by cloning the Bam I/Bal HI restricted PCR product encoding the alpha antigen signal sequence into the Bal I/Bam HI site of PMAO-1. The plasmid pMAO-4 was produced by replacing the Bam HI/Eco RI insert of pMAO-3 with the Bgl II/Eco RI insert used in preparing pMAO-2. A similar set of mouse IL-2 containing plasmids; pRBD-1,2,3 and 4 was produced by replacing the Bam HI/Eco RI rat CDNA insert in each of the respective pMAO plasmids with the PCR dreived Bam HI/Eco RI flanked mouse IL-2 cDNA fragment. All DNA manipulations followed previously described procedures in Maniatis et al., J.Molec. *Cloning: a laboratory Manual*, Cold Spring Harbor Laboratories, Cold Spring, N.Y. (1982). *E. coli* MBM 7070was electroporated with the IL-2 containing BCG/*E. coli* shuttle plasmids and selected on kanamycin (30 ug/ml) LB agar plates. The correct plasmid structures were confirmed on the basis of restriction analysis, DNA sequencing and production of functional IL-2 (see below). *E. coli*-derived plasmids were then used to transform BCG by electroporation according to published procedures (Snapper et al., *Proc. Natl. Acad. Sci. USA* 85:6987–6991 (1988)). BCG colony DNAs were individually tested by PCR for the presence of the IL-2 gene and colony lysates were assayed for expression of functional IL-2 (see below).

Detection of recombinant IL-2. The expression of recombinant IL-2 in BCG was examined by Western and by bioassay. Sonicated BCG lysates and BCG culture medium were electrophoresed on a 17–27% acrylamide gel (Daiichi) and transferred to nitrocellulose. After blocking the membrane with a 15% solution of powdered skim milk, the membrane was incubated overnight with the primary antibody, either rabbit anti-mouse IL-2 (Collaborative Research) or the mouse monoclonal anti-HA tag antibody 12CA5, at a concentration of 1 ug/ml (Wilson et al., *Cell,* 37:76 1984). Peroxidase labelled goat anti-rabbit or goat anti-mouse IgG antibodies (Pierce) were used with a chemiluninescent substrate (Amersham) for detection.

The presence of biologically active IL-2 in bacterial extracts or extracellular media was determined and quantified colorimetrically in a proliferation assay using the IL-2 dependent T cell line CTLL-2 (Mosmann et al., *J. Immun. Methods,* 65:55–63 (1983)). Maximal signals generatd in this assay were similar for either rat or mouse IL-2. *E. coli* and BCG lysates were obtained by sonication of washed bacterial cells in PBS followed by filtration through a 0.22 u filter and dialysis against PBS. No IL-2 inhibitors were found when CTLL-2 cells were incubated with exogenous IL-2 in the presence of extracts prepared from bacteria transformed with the nonproducer plasmid pMV261. To control for differeing growth rates between BCG clones, log-phase BCG were washed and resuspended at an optical density of 0.5 at 600 nm (OD600) in fresh media. At the end of 48 hours, the OD600 was readjusted to 1.0 by diluting the BCG cells with fresh media. The amount of IL-2 in 1 ml (1.0 OD600~2–5x$10^7$ CFU) of cleared supernatant, or in the pellet derived from 1 ml of cells, was then assessed in the proliferation assay.

In vitro spleen cell assay for cytokine production.

Spleens were harvested from 8–12 week old C3H/HeN, C57BL/b or Balb/c mice (Charles River). After mechanical dispersion, the spleen cells were separated by Ficoll/hypaque centrifugation at 200 x g, washed, and placed into RPMI 1640 medium suppliememted with HEPES (N-2-hydroxyethyliperazine-N'-2-ethanesulfonic acid), 10% heat inactivated fetal bovine serum, and 30 ug/ml of kanamycin. Splenocyte assays were performed with either 2 or 4x$10^6$ cells/well (1 ml) in the presence or absence of exogenous murine recombinant IL-2 (Biosource), and either 2x$10^6$ CFU MV261 BCG (wild type BCG or wt BCG), or 2x$10^6$ CFU RBD-4 BCG. Duplicate supernatants were removed at 24 hours and 72 hours, centrifuged and frozen at −70° C. until testing in ELISA assays. Equal spleen cell counts and viabilities were verified prior to final harvest by tryphan blue counting. Equal growth of wt BCG and RBD-4 during the 3-day experiment was verified by measurement of optical density at 600 nm for parallel wells containing supplemental 0.05% tween 80 to prevent bacterial clumping. Cytokine production by spleen cells was measured by commercial ELISA for murine cytokines, which were used according to the manufacturer's instructions. Kits for the detection of murine IL-4,5,6, and TNF-α were purchased from Endogen. The IFN-γ ELISA was obtained from Gibco/BRL. IL-2 was assayed using a kit from Collaborative Research. To detect epitope tagged recombinant mouse IL-2, samples were incubated in wells precoated with rabbit anti-mouse IL-2, washed and reincubated with the murine monoclonal antibody 12CA5 at 1 ug/ml. Bound antibody was detected using peroxidase labelled goat anti-mouse IgG (Pierce et al., *Proc. Natl. Acad. Sci. USA* 85:5678–5682 (1988)).

Results

Construction of BCG Recombinants Producing IL-2

A variety of *E. coli*-BCG shuttle plasmids were constructed to permit production of IL-2 (FIG. 4). A set of plasmids were constructed in which the BCG HSP60 promotor drives the expression of mouse or rat IL-2 (pRBD-1 and pMAo-1). To permit differentiation of the BCG-produced recombinant IL-2 from IL-2 produced by mammalian cells in later experiments, a second set of plasmids was generated that incorporate an influenza hemagglutinin epitope coding sequence at the 5' end of the IL-2 coding sequence to produce an epitope-tagged IL-2 molecule (pRBD-2 and pMAO2). To allow secretion of the recombinant IL-2 molecules, the secretion signal sequence of the mycobacterial alpha-antigen was added to the 5' end of the IL-2 coding sequence in a third set of plasmids (pRBD3 and pMAO-3). A fourth set of plasmids contained both the epitope tag and the secretion signal sequence upstream of IL-2 (pRBD-4 and pMAO-4). All constructs containing the IL-2 gene were found to produce biologically active IL-2 in *E. coli.*

BCG cells were transformed with all of the recombinant plasmids. The BCG transformation efficiency for both the parental pMV261 and the constructs containing the alpha antigen signal sequence were on the order of 10–100 times greater than those IL-2 constructs lacking the signal sequence. This was a uniform finding occurring in both mouse and rat IL-2 containing constructs and may be due to a selective disadvantage caused by the intracellular accumulation of this foreign protein.

IL-2 Production and Secretion by BCG Transformants

Figure 5A:
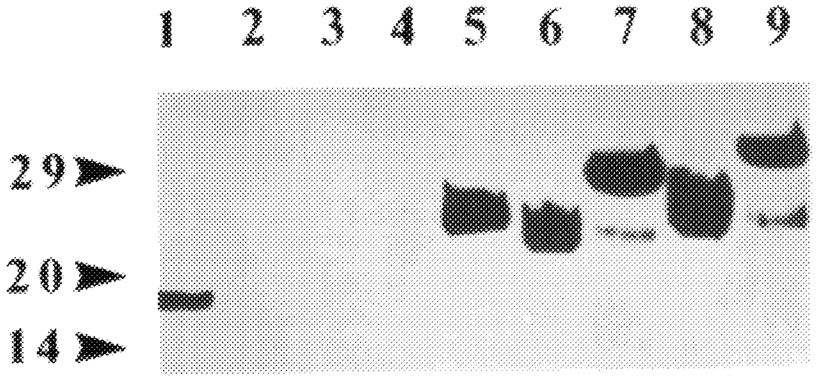
FIG. 5A is a western blot of BCG pellet (PLT) lysates and BCG culture supernatants (SN) from RBD recombinants detected with polyclonal rabbit anti-murine IL-2 antibody; Lane 1=recombinant murine IL-2, Lanes 2&3=MV261PLT and SN, Lanes 4&5=RBD-2 PLT and SN, Lanes 6&7= RBD-3 PLT and SN, Lanes 8&9=RBD-4 PLT and SN respectively
Figure 5B:
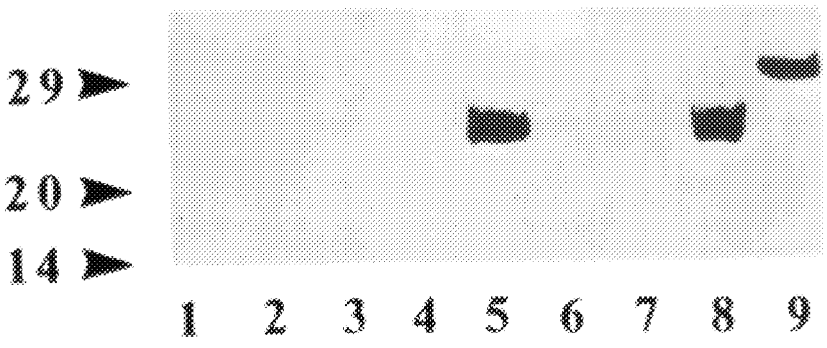
FIG. 5B is the identical western blot in FIG. 5*a* which was reprobed with mmurine monoclonal antibody 12CA5 specific for the influenza epitope tag

The expression of IL-2 protein by representative BCG recombinants was assayed by probing Western blots with antibodies directed against IL-2 (FIG. 5A) or against the influenza hemagglutinin epitope (FIG. 5B). BCG recombinants that expressed IL-2 without a secretion signal sequence accumulated a single form of IL-2 intracellularly (FIG. 5A, lane 5), but no IL-2 extracellularly (FIG. 5A, lane 4). High and low molecular weight forms of IL-2 accumulated in BCG recombinants that expressed IL-2 linked to the secretion signal (FIG. 5A, lanes 7–9); only the lower molecular weight form was found in the supernatant, consistent with the cleavage of the signal sequence during secretion (FIG. 5A, lanes 6 and 8). The recombinant IL-2 proteins that contain the influenza hemagglutinin epitope tag can also be visualized with a monoclonal antibody specific for the tag (FIG. 5B, lanes 5, 8 and 9).

Figure 6:
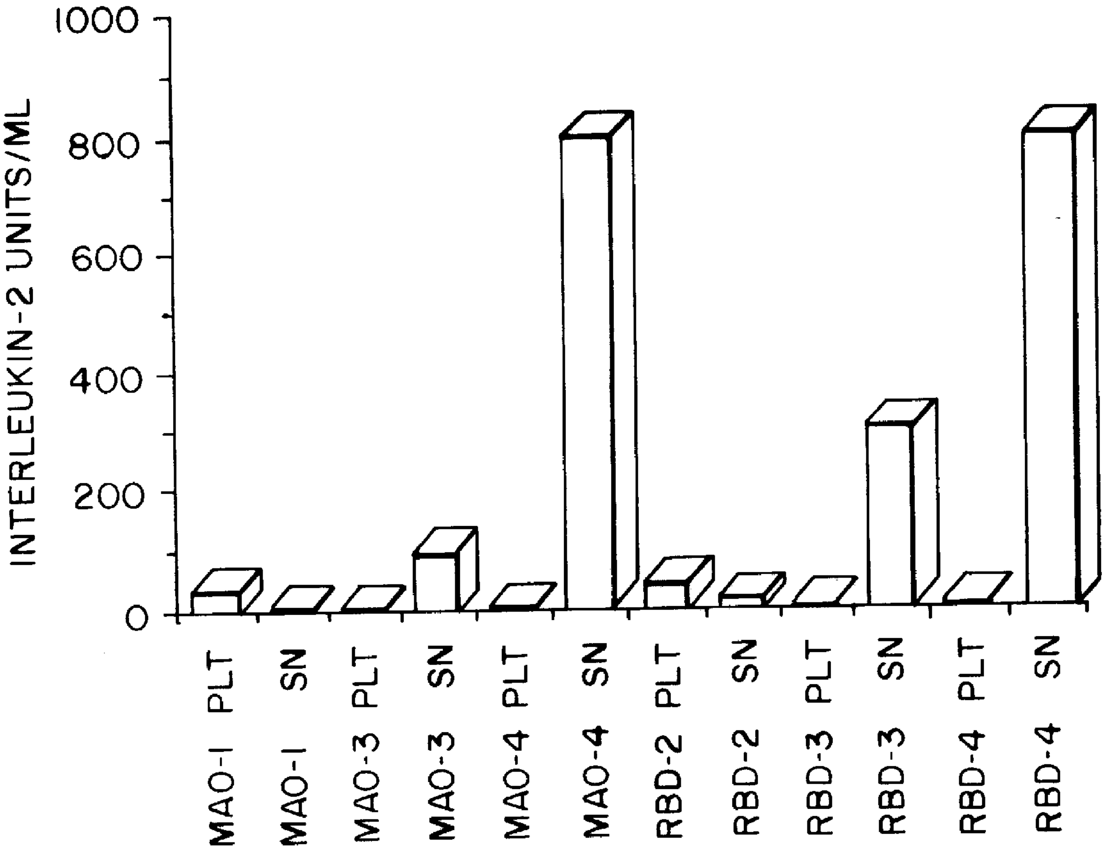
FIG. 6 is a graphic representation of expression of biologically active IL-2 in BCG pellet (PLT) lysates and BCG culture supernatants (SN) from rat (MAO) and mouse (RBD) recombinant BCG clones.
Figure 7A:
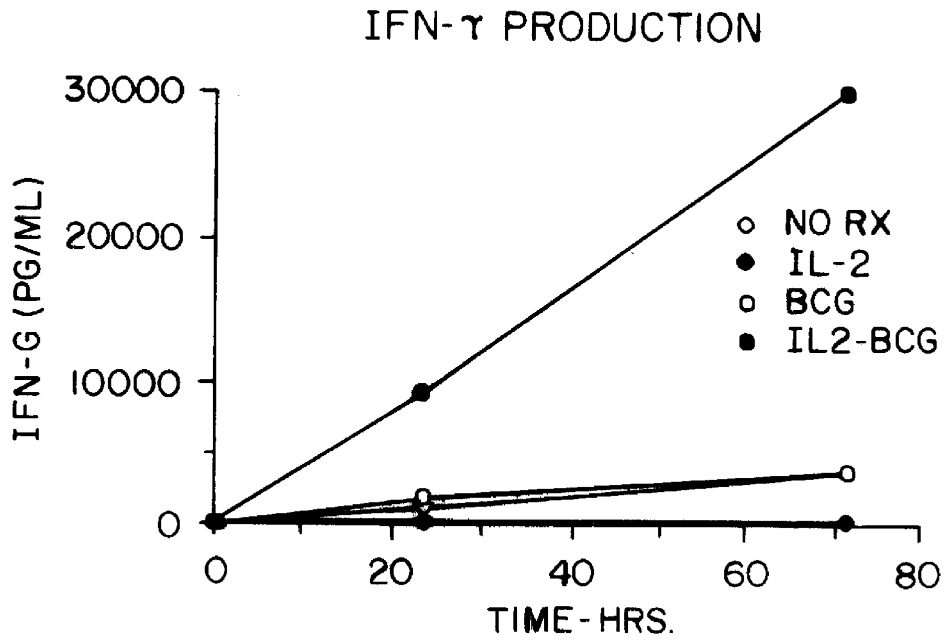
FIG. 7A is a graphic representation of the time course of splenocyte interferon-γ production, in response to incubation alone (no Rx), or with IL-2 (IL-2), wild type BCG (BCG), or recombinant IL-2 secreting BCG (IL2-BCG). 2500 pg/ml of recombinant IL-2 was present at time zero in the IL2 group. The amount of IL-2 present in the IL2-BCG group includes that produced by the recombinant BCG and that produced by splenocytes.
Figure 7B:
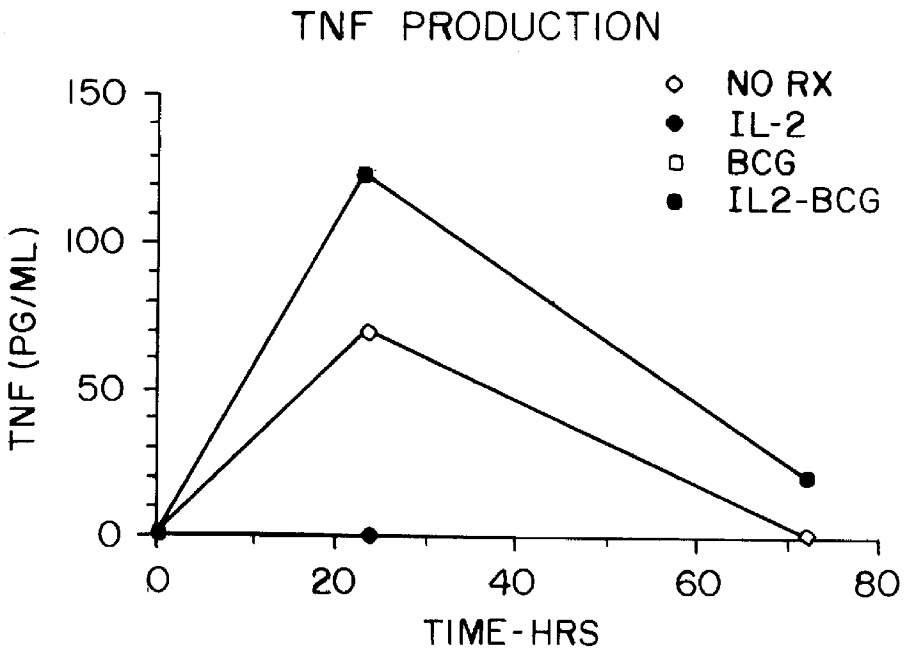
FIG. 7B is a graphic representation of the time course of the splenocyte tumor necrosis factor production, in response to incubation alone (no Rx), or with IL-2 (IL-2), wild type BCG (BCG), or recombinant IL-2 secreting BCG (IL2-BCG). 2500 pg/ml of recombinant IL-2 was present at time zero in the IL2 group. The amount of IL-2 present in the IL2-BCG group includes that produced by the recombinant BCG and that produced by splenocytes.
Figure 7C:
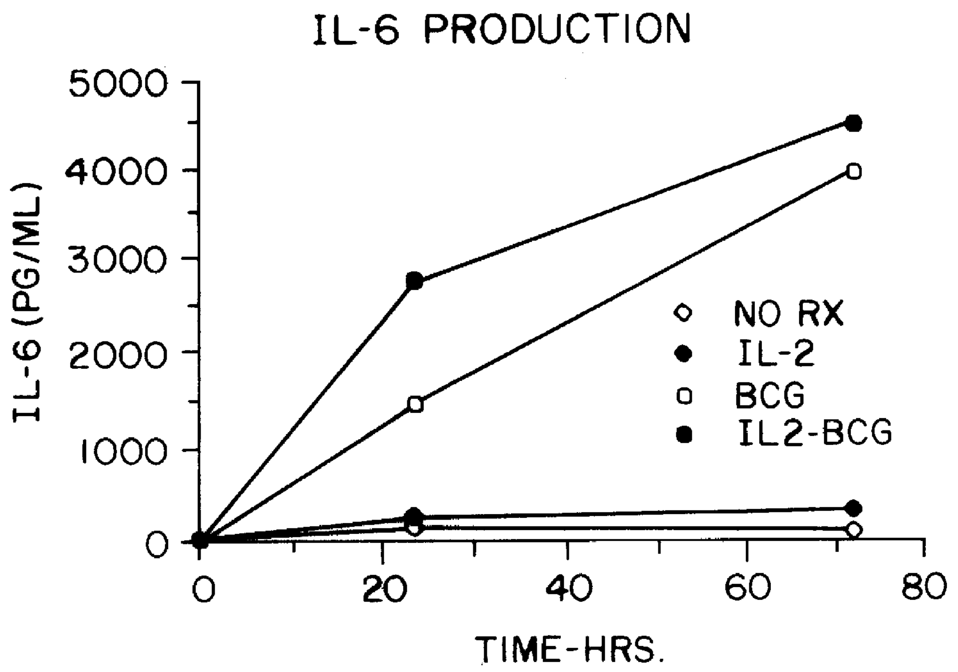
FIG. 7C is a graphic representation of the time course of the splenocyte interleukin-6 production, in response to incubation alone (no Rx), or with IL-2 (IL-2), wild type BCG (BCG), or recombinant IL-2 secreting BCG (IL2-BCG). 2500 pg/ml of recombinant IL-2 was present at time zero in the IL2 group. The amount of IL-2 present in the IL2-BCG group includes that produced by the recombinant BCG and that produced by splenocytes.
Figure 7D:
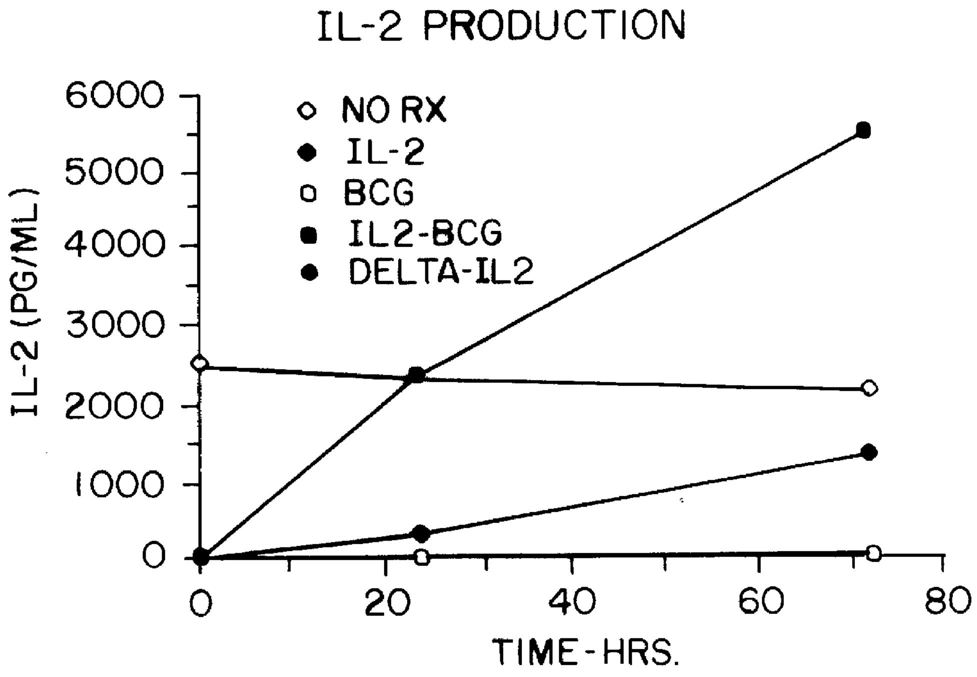
FIG. 7D is a graphic representation of the time course of the total interleukin-2 production, in response to incubation alone (no Rx), or with IL-2 (IL-2), wild type BCG (BCG), or recombinant IL-2 secreting BCG (IL2-BCG). 2500 pg/ml of recombinant IL-2 was present at time zero in the IL2 group. The amount of IL-2 present in the IL2-BCG group includes that produced by the recombinant BCG and that produced by splenocytes. Delta-IL2, representing endogenous IL-2 produced by splenocytes was computed by subtracting the total IL-2 from the parallel experiment in-which splenocytes were omitted.

The expression of IL-2 protein by representative BCG recombinants was also investigated using an IL-2-dependent proliferation assay (FIG. 6). Most of the biologically active IL-2 produced by clones MAO-1 and RBD-2 was located in the pellet while most of the IL-2 product from clones MAO-3, MAO-4, RBD-3 and RBD-4 was found in the extracellular media. BCG clones expressing IL-2 linked to the alpha antigen signal peptide (MAO-3, MAO-4, RBD-3 and RBD-4) produced significantly more biologically active IL-2 than those clones without the signal peptide (MAO-1 and RBD-2). Both mouse and rat IL-2 BCG recombinants expressed similar amounts of bioactive IL-2. The amounts of recombinant mouse IL-2 in pellets and in supernatants were also measured by an ELISA and similar results were obtained.

Stimulation of Solenocyte Cytokine Production Using BCG-IL-2 Recombinants

To evaluate the immunostimulatory properties of IL-2 secreting BCG, the ability of BCG recombinants to alter the levels of cytokines IL-2, 4, 5, 6, TFN-α and γ-IFN produced by cultured murine spleen cells was investigated (FIG. 7). Splenocytes derived from C3H/HeN mice were incubated with either no BCG, 25 units/ml of IL-2, MV261 (wt)BCG or RBD-4 BCG. The levels of specific cytokines in the tissue culture media were measured by ELISA at 24 and 72 hours after the start of the experiment.

The data in FIG. 7 shows that no significant basal cytokine expression was detected from splenocytes in the absence of BCG or exogenous IL-2. In the IL-2 treated group, there was a modest elevation in IFN-γ production over the time course of the experiment, but no detectable increases in other cytokines. By contrast, splenocytes exposed to BCG produced significant amounts of IL-6, TFN-α and IFN-γ. However, the most significant cytokine production was observed with splenocytes exposed to BCG recombinants secreting IL-2. Substantially higher levels of IFN-γ were produced when spleen cells were exposed to recombinant BCG than when they were exposed to nonrecombinant BCG. Endogenous IL-2 production, as calculated by subtracting the total IL-2 in the absence of splenocytes from the total IL-2 in the presence of splencoytes (FIG. 7, delta IL-2), also appeared to increase significantly. Finally, there was a more modest increase in TFN-α and IL-6 levels when spleen cells were exposed to recombinant BCG. We did not detect significant amounts of either IL-4 or IL-5 in these splenocyte cultures (lower assay limit 100 ug/ml) under any of these experimental conditions.

Figure 8A:
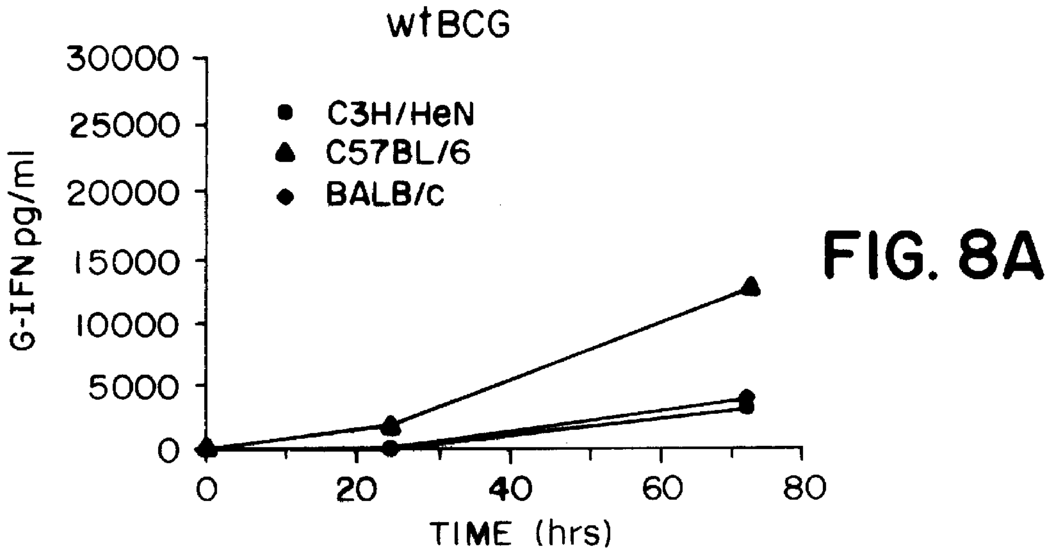
FIG. 8A is a graphic representation of interferon-γ production by splenocytes derived from 3 mouse strains: C3H/HeN, C57BL/6 and BALB/c in response to wild type BCG (wtBCG).
Figure 8B:
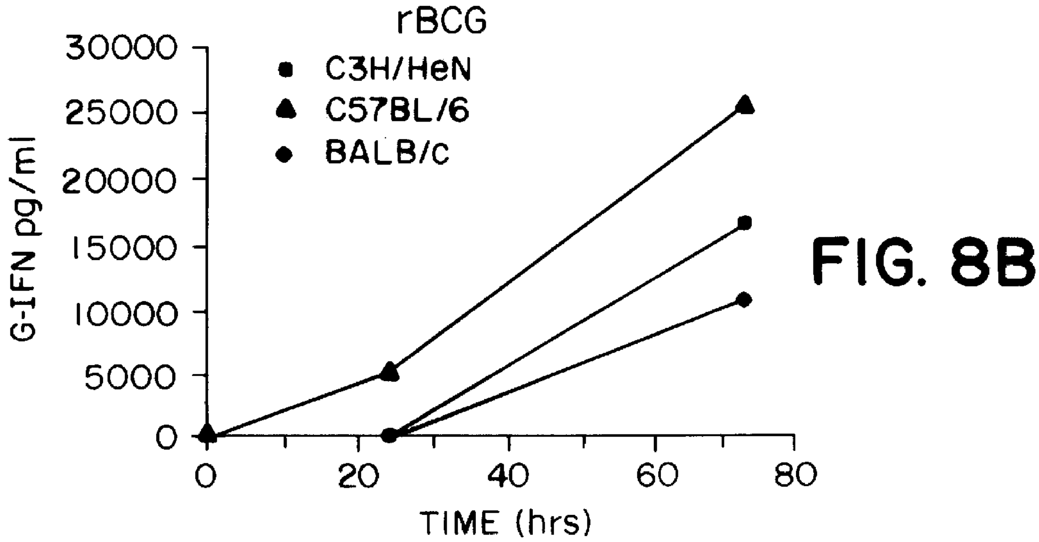
FIG. 8B is a graphic representation of interferon-γ production by splenocytes derived from 3 mouse strains: C3H/HeN, C57BL/6 and BALB/c in response to recombinant IL-2 secreting BCG (rBCG).
Figure 8C:
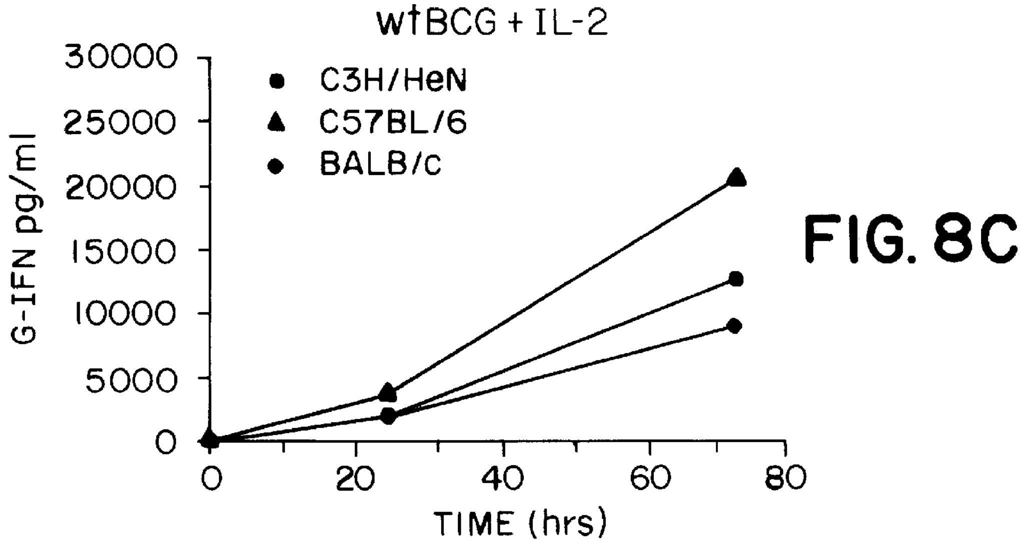
FIG. 8C is a graphic representation of interferon-γ production by splenocytes derived from 3 mouse strains: C3H/HeN, C57BL/6 and BALB/c in response exogenous IL-2 (25 units=2500 pg) plus wtBCG.

There is a marked genetic variation in the amount of IFN-γ and IL-2 produced by splenocytes derived from mice infected by BCG (Huygen et al., *Infect. Immun.* 60:2880–2886 (1992)). For example, splenocytes from BCG-infected C57BL/6 mice produce high levels of IFN-γ and IL-2 while splenocytes from BCG-infected BALB/c mice produce low levels of these two cytokines after stimulation in vitro. To determine whether the enhanced immunostimulatory properties of IL-2 secreting BCG were strain independent, splenocytes were isolated from three different mouse strains, exposed to wild type or recombinant BCG, and the levels of specific cytokines in the tissue culture media were measured by ELISA at 24 and 72 hours. The results are shown in FIG. 8. As in the previous experiment, there was very little IFN-γ production by C3H/HeN splenocytes stimulated with wtBCG (FIG. 8A), but substantial levels were observed when the C3H/HeN splenocytes were stimulated with recombinant BCG (rBCG) producing IL-2 (FIG. 8B). Enhanced stimulation was also observed with BALB/c and C57BL/6 splenocytes exposed to rBCG, although the levels of IFN-γ production were somewhat less with BLAB/c and somewhat greater with C57BL/6. Similar results were obtained if exogenous IL-2 was added in the presence of wild type BCG (FIG. 8C). There was no detectable IL-4 production in these splenocyte cultures. These results indicate that the enhanced immunostimulatory properties of IL-2 secreting BCG are not strain dependent.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of inducing an immune response in a mammalian host against one or more pathogens, comprising administering to the host a live, recombinant mycobacterium, the recombinant mycobacterium having incorporated therein a plasmid comprising:

DNA of interest encoding at least one protein antigen for each of said pathogens fused to a mycobacterial heat shock gene promoter or a mycobacterial stress protein gene promoter and translational start site in such a manner that expression of the DNA of interest is under the control of the promoter, wherein the protein antigen is produced by the recombinant mycobacterium replicating in the host.

2. A method of claim 1 wherein the recombinant mycobacterium is selected from the group consisting of:

a. *Mycobacterium smegmatis;* b. *Mycobacterium bovis*-BCG;

c. *Mycobacterium avium;* d. *Mycobacterium phlei;* e. *Mycobacterium fortuitum;* f. *Mycobacterium lufu;* g. *Mycobacterium paratuberculosis;* h. *Mycobacterium habana;* i. *Mycobacterium scrofulaceiu;* j. *Mycobacterium intracellulare;* k. *Mycobacterium tuberculosis*; and l. any genetic variants thereof.

3. A method of claim 2 wherein the DNA of interest encodes at least one protein antigen selected from the group consisting of,: HIV gag, HIV Mol, HIV env, SIV gag, SIV pol and SIV env.

4. A method of claim 1 further comprising co-administering a protein antigen for each of said pathogens.

5. A vaccine comprising a live, recombinant mycobacterium having DNA of interest which is expressed extrachromosomally under the control of a mycobacterial heat shock gene promoter or a mycobacterial stress protein gene promoter and an appropriate carrier.

* * * * *

UNITED STATES PATENT AND TRADEMARK OFFICE

CERTIFICATE OF CORRECTION

PATENT NO. : 5,830,475

DATED : November 3, 1998

INVENTOR(S) : Anna Aldovini and Richard A. Young

It is certified that error appears in the above-identified patent and that said Letters Patent is hereby corrected as shown below:

Column 1, line 24 after "Public Health Service" insert --, NIH Grant No. AI-26463--.

Column 1, line 24 after "World Health Organization." insert --The Government has certain rights in the invention.--

In column 24, line 42, delete the term "Mol" and insert --pol--.

Signed and Sealed this

First Day of June, 1999

Attest:

Q. TODD DICKINSON

Attesting Officer

*Acting Commissioner of Patents and Trademarks*